United States Patent
Jones, Jr.

(10) Patent No.: US 10,045,532 B2
(45) Date of Patent: Aug. 14, 2018

(54) SYNERGISTIC HERBICIDAL MIXTURES FOR GLYPHOSATE-RESISTANT VOLUNTEER CORN CONTROL

(71) Applicant: Valent U.S.A., Corporation, Walnut Creek, CA (US)

(72) Inventor: Ronald S. Jones, Jr., Allen, TX (US)

(73) Assignee: VALENT U.S.A., CORPORATION, Walnut Creek, CA (US)

( * ) Notice: Subject to any disclaimer, the term of this patent is extended or adjusted under 35 U.S.C. 154(b) by 4 days.

(21) Appl. No.: 15/203,962

(22) Filed: Jul. 7, 2016

(65) Prior Publication Data

US 2017/0006873 A1    Jan. 12, 2017

Related U.S. Application Data

(60) Provisional application No. 62/189,557, filed on Jul. 7, 2015.

(51) Int. Cl.
*A01N 43/54*  (2006.01)
*A01N 57/20*  (2006.01)

(52) U.S. Cl.
CPC ..................... *A01N 43/54* (2013.01)

(58) Field of Classification Search
None
See application file for complete search history.

(56) References Cited

U.S. PATENT DOCUMENTS

2009/0233796 A1* 9/2009 North .................. A01N 43/54
                                                            504/243
2010/0234230 A1* 9/2010 Fowler ................ A01N 25/04
                                                            504/289

OTHER PUBLICATIONS

Ikley, Joseph. The utility of saflufenacil on glyphosate-resistant horseweed and its effect on select soybean varieties. Diss. 2012.*
Ikley, Joseph. The utility of saflufenacil on glyphosate-resistant horseweed and its effect on select soybean varieties. Diss. 2012.*

* cited by examiner

*Primary Examiner* — Alton N Pryor
(74) *Attorney, Agent, or Firm* — Wood, Phillips, Katz, Clark & Mortimer

(57) ABSTRACT

The present invention relates to methods for enhancing the herbicidal activity of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, and ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and to methods for controlling volunteer glyphosate-resistant corn comprising applying synergistic mixtures of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof and glyphosate, or a salt thereof, to an area where volunteer glyphosate-resistant corn is growing.

12 Claims, No Drawings

SYNERGISTIC HERBICIDAL MIXTURES FOR GLYPHOSATE-RESISTANT VOLUNTEER CORN CONTROL

FIELD OF THE INVENTION

The present invention generally relates to synergistic mixtures for control of volunteer corn that is glyphosate-resistant.

BACKGROUND OF THE INVENTION

Crop growers struggle to control volunteer plants that express a gene imparting glyphosate tolerance/glyphosate resistance in fields of glyphosate-resistant crop plants. Glyphosate is a popular and effective herbicide that is an inhibitor of 5-enolpyruvylshikimate-3-phosphate synthase. One disadvantage of glyphosate is that it can cause crop injury if applied after the crop plants are planted.

By using recombinant DNA technology, Monsanto Company (St. Louis, Mo.) has developed glyphosate-resistant crop plants, such as soybeans, corn, cotton, wheat, canola, sugarbeet, rice and lettuce. Cultivating glyphosate-resistant crops allows growers to apply glyphosate to the crop growing areas after the crop plants are planted without risking crop injury.

One issue that has emerged as a result of this technology is that due to crop rotation, glyphosate-resistant seeds from the previous season can germinate and contaminate the field the following season. For example, glyphosate-resistant corn seeds that fall to the ground during harvest may remain dormant over the winter and then germinate the following spring after crop growers have planted a different crop plant, such as soybeans, in the same field. Corn plants/weeds, or "volunteer" corn, that grow in the soybean field cannot be controlled with glyphosate treatments (such as RoundUp®, available from Monsanto Company, RoundUp is a registered trademark of Monsanto Technology LLC).

The volunteer crops cause the same problems that non-genetically modified weeds do they steal valuable resources from the crop plants. By reducing the available sunlight, soil nutrients, and moisture, the volunteer crops/weeds can drastically reduce crop yields.

Another class of herbicides, "PPO inhibitors," work by inhibiting protoporphyrinogen oxidase ("PPO"). PPO is an enzyme that oxidizes protoporphyrinogen which disrupts the chlorophyll synthesis pathway thereby reducing photosynthesis. PPO inhibitors typically are not effective against grasses after they have germinated.

Accordingly, there is a need in the art for new methods for controlling volunteer corn that is resistant to glyphosate. The methods should have a low risk of allowing the glyphosate-resistant corn to become resistant to other chemistries. The methods should also not be phytotoxic to the crop plants or cause reductions in crop yields.

SUMMARY OF THE INVENTION

In one aspect, the present invention is directed to methods for enhancing the herbicidal activity of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, comprising applying synergistic mixtures of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, and glyphosate, or a salt thereof, to an area where volunteer glyphosate-resistant corn is growing, wherein the rate of application of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare, and the rate of application of glyphosate, or a salt thereof, is from about 0.0001 to about 5,000 grams per hectare.

In another aspect, the present invention is directed to methods for controlling volunteer glyphosate-resistant corn comprising applying synergistic mixtures of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, to an area where volunteer glyphosate-resistant corn is growing, wherein the rate of application of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare, and the rate of application of glyphosate, or a salt thereof, is from about 0.0001 to about 5,000 grams per hectare.

In a further aspect, the present invention is directed to methods for controlling glyphosate-resistant weeds comprising applying synergistic mixtures of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, to an area where glyphosate-resistant weeds are growing, wherein the rate of application of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare, and the rate of application of glyphosate, or a salt thereof, is from about 0.0001 to about 5,000 grams per hectare.

DETAILED DESCRIPTION OF THE INVENTION 2-((3-(2-Chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, and ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate are PPO inhibitors having the following structures:

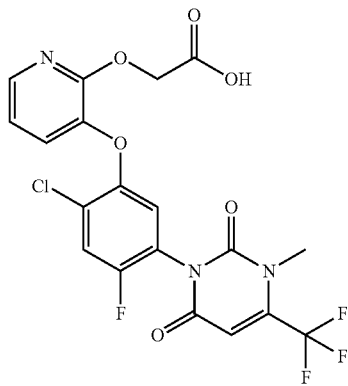 [SMILES: Cn1c(C(F)(F)F)cc(=O)n(-c2cc(Oc3cccnc3OCC(=O)O)c(Cl)cc2F)c1=O]

2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid;

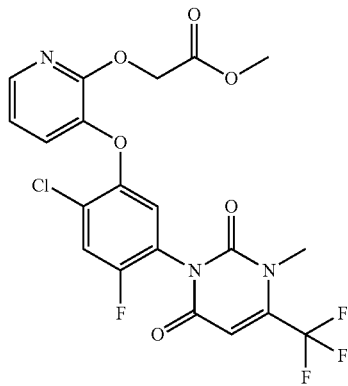 [SMILES: COC(=O)COc1ncccc1Oc1cc(-n2c(=O)cc(C(F)(F)F)n(C)c2=O)c(F)cc1Cl]

methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate; and

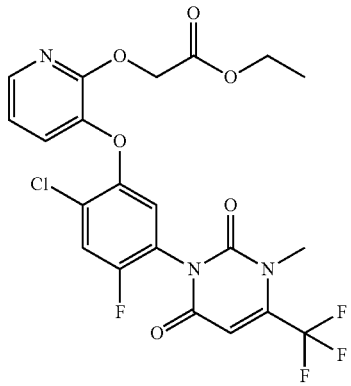 [SMILES: CCOC(=O)COc1ncccc1Oc1cc(-n2c(=O)cc(C(F)(F)F)n(C)c2=O)c(F)cc1Cl]

ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate.

Unexpectedly, Applicant determined that when ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate is applied at a rate of from about 0.001 to about 100 grams per hectare and glyphosate is applied at a rate of from about 0.0001 to about 5,000 grams per hectare the glyphosate enhances the activity of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and is highly effective at controlling emerged volunteer corn that is resistant to glyphosate. Most PPO herbicides have no post emergent activity against members of the grass family, such as corn. Therefore, one of skill in the art would not have been able to predict that a PPO herbicide when combined with glyphosate would kill emerged corn that is resistant to glyphosate when glyphosate is applied alone. One of skill in the art would have expected the volunteer glyphosate-resistant corn to survive treatment with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate. In contrast to the expected result, synergistic mixtures of the present invention provided up to 100% control of emerged volunteer corn (see, for example, Example 1 below).

In one embodiment, the present invention is directed to methods for enhancing the herbicidal activity of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, comprising applying a synergistic mixture of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, and glyphosate, or a salt thereof, to an area where volunteer glyphosate-resistant corn is growing, wherein the rate of application of 2-((3-(2-chloro-4-fluoro-5-(3-methyl-2,6-dioxo-4-(trifluoromethyl)-2,3-dihydropyrimidin-1(6H)-yl)

phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare, and the rate of application of glyphosate, or a salt thereof, is from about 0.0001 to about 5,000 grams per hectare.

In a preferred embodiment, the compound is ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate.

In another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, and ethyl [3-[2-chloro-4-fluoro-5-(1-methyl-6-trifluoromethyl-2,4-dioxo-1,2,3,4-tetrahydropyrimidin-3-yl)phen oxy]-2-pyridyloxy]acetate, or a combination thereof, and glyphosate, or a salt thereof, are applied to enhance the herbicidal activity of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, from about 0.01 to about 50 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phen oxy]-2-pyridyloxy]acetate, or a combination thereof, is applied to the area where the volunteer glyphosate-resistant corn is growing. In a preferred embodiment, from about 0.5 to about 20 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is applied with glyphosate, or a salt thereof, to the area where the volunteer glyphosate-resistant corn is growing.

In a further embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to enhance the herbicidal activity of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, from about 10 to about 2,500 grams per hectare of glyphosate, or a salt thereof, is applied to the area where the volunteer glyphosate-resistant corn is growing. In a preferred embodiment, from about 10 to about 2,000 grams per hectare of glyphosate is applied with 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, to the area where the volunteer glyphosate-resistant corn is growing. In alternative embodiment, from about 100 to about 2,000 grams per hectare of glyphosate, or a salt thereof, is applied with 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, to the area where the volunteer glyphosate-resistant corn is growing.

In an alternative embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, and glyphosate, or a salt thereof, are applied to enhance the herbicidal activity of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, from about 500 to about 5,000 grams per hectare of glyphosate, or a salt thereof, is applied to the area where the volunteer glyphosate-resistant corn is growing. In a preferred embodiment, from about 500 to about 2,500 grams per hectare of glyphosate, or a salt thereof, is applied with 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, to the area where the volunteer glyphosate-resistant corn is growing. In a more preferred embodiment, from about 500 to about 2,000 grams per hectare of glyphosate, or a salt thereof, is applied with 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, to the area where the volunteer glyphosate-resistant corn is growing.

In a further embodiment, the glyphosate salt is selected from the group consisting of a potassium salt, a sodium salt, an isopropylamine salt, a trimesium salt, an ammonium salt, and a diammonium salt. In a preferred embodiment, the glyphosate salt is potassium.

In yet another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phen oxy]-2-pyridyloxy]acetate, and a combination thereof, and glyphosate, or a salt thereof, are applied to enhance the herbicidal activity of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, a glyphosate-resistant crop plant is growing in the area where the volunteer glyphosate-resistant corn is growing. In a preferred embodiment, the glyphosate-resistant crop plant is selected from the group consisting of soybeans, cotton, wheat, canola, sugarbeet, rice and lettuce. In a more preferred embodiment, the glyphosate-resistant crop plant is soybeans.

In an alternative embodiment, the present invention is directed to methods for controlling volunteer glyphosate-resistant corn comprising applying a synergistic mixture of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, to an area where volunteer glyphosate-resistant corn is growing, the rate of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare and the rate of glyphosate, or a salt thereof, is from about 0.0001 to about 5,000 grams per hectare.

In another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control volunteer glyphosate-resistant corn, from about 0.01 to about 50 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is applied to the area where the volunteer glyphosate-resistant corn is growing. In a preferred embodiment, from about 0.5 to about 20 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is applied with glyphosate, or a salt thereof, to the area where the volunteer glyphosate-resistant corn is growing.

In a preferred embodiment, the compound is ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate.

In a further embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phen oxy]-2-pyridyloxy]acetate, or a combination thereof, and glyphosate, or a salt thereof, are applied to control volunteer glyphosate-resistant corn, from about 10 to about 2,500 grams per hectare of glyphosate, or a salt thereof, is applied to the area where the volunteer glyphosate-resistant corn is growing. In a preferred embodiment, from about 10 to about 2,000 grams per hectare of glyphosate, or a salt thereof, is applied with 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, to the area where the volunteer glyphosate-resistant corn is growing. In an alternative embodiment, from about 100 to about 2,000 grams per hectare of glyphosate, or a salt thereof, is applied with a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, to the area where the volunteer glyphosate-resistant corn is growing.

In yet another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control volunteer glyphosate-resistant corn, a glyphosate-resistant crop plant is growing in the area where the volunteer glyphosate-resistant corn is growing. In a preferred embodiment, the glyphosate-resistant crop plant is selected from the group consisting of soybeans, cotton, wheat, canola, sugarbeet, rice and lettuce. In a more preferred embodiment, the glyphosate-resistant crop plant is soybeans.

In yet another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control volunteer glyphosate-resistant corn, the volunteer glyphosate-resistant corn is also resistant to 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and a glyphosate-resistant crop plant is growing in the area where the volunteer glyphosate-resistant corn is growing. In a preferred embodiment, the glyphosate-resistant crop plant is selected from the group consisting of soybeans, cotton, wheat, canola, sugarbeet, rice and lettuce. In a more preferred embodiment, the glyphosate-resistant crop plant is soybeans.

In an alternative embodiment, the present invention is directed to methods for controlling glyphosate-resistant weeds comprising applying a synergistic mixture of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate to an area where glyphosate-resistant weeds are growing, the rate of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is from about 0.001 to about 100 grams per hectare, and the rate of glyphosate, or a salt thereof, is from about 0.0001 to about 5,000 grams per hectare.

In another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control glyphosate-resistant weeds, from about 0.01 to about 50 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is applied to the area where the glyphosate-resistant weeds are growing. In a preferred embodiment, from about 0.5 to about 20 grams per hectare of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, or a combination thereof, is applied to the area where the glyphosate-resistant weeds are growing.

In a further embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control glyphosate-resistant weeds, from about 10 to about 2,500 grams per hectare of glyphosate, or a salt thereof, is applied to the area where the glyphosate-resistant weeds are growing. In a preferred embodiment, from about 10 to about 2,000 grams per hectare of glyphosate, or a salt thereof, is applied to the area where the glyphosate-resistant weeds are growing. In an alternative embodiment, from about 100 to about 2,000 grams per hectare of glyphosate, or a salt thereof, is applied to the area where the glyphosate-resistant weeds are growing.

In yet another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control glyphosate-resistant weeds, a glyphosate-resistant crop plant is growing in the area where the glyphosate-resistant weeds are growing. In a preferred embodiment, the glyphosate-resistant crop plant is selected from the group consisting of soybeans, cotton, wheat, canola, sugarbeet, rice and lettuce. In a more preferred embodiment, the glyphosate-resistant crop plant is soybeans.

In yet another embodiment, when a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, are applied to control glyphosate-resistant weeds, the glyphosate-resistant weeds are also resistant to 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, or ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a glyphosate-resistant crop plant is growing in the area where the weeds are growing. In a preferred embodiment, the glyphosate-resistant crop plant is selected from the group consisting of soybeans, cotton, wheat, canola, sugarbeet, rice and lettuce. In a more preferred embodiment, the glyphosate-resistant crop plant is soybeans.

In another embodiment, the glyphosate-resistant weed is selected from the group consisting of *Lolium multiflorum, Amaranthus palmeri, Amaranthus rudis, Amaranthus tuberculatus, Ambrosia artemisiifolia*, and *Kochia scoparia*.

In another embodiment, the present invention is directed to methods for using the mixtures of the present invention by diluting the mixtures with water, and then applying the diluted mixtures to the area where the volunteer glyphosate-resistant corn is growing. For example, the mixtures can be formulated to be compatible with a tank mixer. As used herein, a "tank mixer" refers to tank where agricultural formulations are mixed with water prior to application. For example, the tank mixer may be mounted to a tractor-drawn fluid dispensing system.

In a further embodiment, a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, is applied to provide long-term synergistic activity against glyphosate-resistant weeds.

For example, 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid and glyphosate, or a salt thereof, may be applied to crops using methods known by those of skill in the art. The plants may be glyphosate-resistant and/or glufosinate-resistant corn plants. Rates of application within the scope of the present invention may be used.

In another example, 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid and glyphosate, or a salt thereof, may be applied to glyphosate-resistant weeds selected from the group consisting of *Lolium multiflorum, Amaranthus palmeri, Amaranthus rudis, Amaranthus tuberculatus, Ambrosia artemisiifolia*, and *Kochia scoparia* by methods known by those of skill in the art. Rates of application within the scope of the present invention may be used.

In another example, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate and glyphosate, or a salt thereof, may be applied to crops using methods known by those of skill in the art. The plants may be glyphosate-resistant and/or glufosinate-resistant corn plants. Rates of application within the scope of the present invention may be used.

In yet another example, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate and glyphosate, or a salt thereof, may be applied to glyphosate-resistant weeds selected from the group consisting of *Lolium multiflorum, Amaranthus palmeri, Amaranthus rudis, Amaranthus tuberculatus, Ambrosia artemisiifolia*, and *Kochia scoparia* by methods known by those of skill in the art. Rates of application within the scope of the present invention may be used.

In a further example, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate, or a salt thereof, may be applied to crops using methods known by those of skill in the art. The plants may be glyphosate-resistant and/or glufosinate-resistant corn plants. Rates of application within the scope of the present invention may be used.

In another example, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate, or a salt thereof, may be applied to glyphosate-resistant weeds selected from the group consisting of *Lolium multiflorum, Amaranthus palmeri, Amaranthus rudis, Amaranthus tuberculatus, Ambrosia artemisiifolia*, and *Kochia scoparia* by methods known by those of skill in the art. Rates of application within the scope of the present invention may be used.

As used herein, "enhancing the herbicidal activity of a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof" means that the synergistic rates allow for a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, and ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate to be more effective than when applied without glyphosate (or a salt thereof), or with glyphosate outside of the synergistic rates claimed herein.

In another embodiment, the mixtures of the present invention are mixed with another agricultural active ingredient in a tank mixer before being applied to the field. Examples of other agricultural active ingredients suitable for mixing with the formulations of the present invention include herbicides, pesticides and plant growth regulators.

As used herein, "controlling volunteer glyphosate-resistant corn" means that the negative impact of the volunteer glyphosate-resistant corn on the crop plant is reduced to a level that is desirable to the crop grower.

As used herein, "controlling glyphosate-resistant weeds" means that the negative impact of the glyphosate-resistant weeds on the crop plant is reduced to a level that is desirable to the crop grower.

As used herein, "crop plant" refers to a glyphosate-resistant plant that is cultivated and harvested to produce food, clothing, fuel, or for another economically important use. When referring to control of volunteer glyphosate-resistant corn, "crop plant" excludes corn. Examples of crop plants include soybeans, cotton, wheat, canola, sugarbeet, rice and lettuce.

As used herein, "volunteer" crop refers to a genetically-modified crop plant that expresses a gene that provides glyphosate tolerance/resistance that is growing in an undesirable location. For example, "volunteer" corn may be growing in a field where a crop grower has planted soybeans.

As used herein, "long-term synergistic activity" means that a compound selected from the group consisting of 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetic acid, methyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate, and a combination thereof, and glyphosate, or a salt thereof, control emerged volunteer glyphosate-resistant corn or weeds for more than 14 days after treatment. The synergistic activity is not limited to a temporary increase in symptoms of herbicidal activity, but is sufficient ro continue until the end of the crop season.

As used herein, "plant" refers to at least one plant.

As used herein, "weed" refers to a plant that is growing in an undesirable location and competing with a crop plant for resources.

As used herein, the "area where volunteer glyphosate-resistant corn is growing" refers to any location, such as a field or growing medium, where the volunteer corn is located while alive. This area is equivalent to where the crop plant is located.

As used herein, "post emergence" or "post emergent" refers to an herbicide treatment that is applied to an area after the weeds or volunteer crop plants have germinated and emerged from the ground or growing medium, with or without crop plants present.

Throughout the application, the singular forms "a," "an," and "the" include plural reference unless the context clearly dictates otherwise.

Throughout the application, "glyphosate-resistant" and "glyphosate-tolerant" are used interchangeably.

Glyphosate may be used in the form of a salt. For example, as the ammonia, organic amine, or alkali metal salt. Suitable glyphosate salts include the ethonolamine, isopropylamine, dimethylethanolamine, sodium, potassium, and lithium salts.

As used herein, synergy means that when combined, the claimed mixture achieves a result that would not be obtained by the individual components or by another combination of the individual components. The mixtures of the present invention display unexpected synergy because one of skill in the art would not have expected to find that the combination of the two compounds leads to such an effective reduction in unwanted volunteer glyphosate-resistant corn plants or glyphosate-resistant weeds.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The invention will be understood more clearly from the following non-limiting representative examples. Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLES

Example 1

Glyphosate-resistant corn was foliarly sprayed with mixtures of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and the potassium salt of glyphosate in outdoor replicated field plots. The corn was at the V4 (plants with four leaves with visible collars, about 6 to 8 inches tall) stage of development at the time of treatment. Roundup® PowerMax (available from Monsanto Company) was used as the source of the potassium salt of glyphosate. The adjuvant crop oil concentrate was applied with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate. The effects of the treatments were observed and recorded 9 and 23 days after the treatments ("9 DAT" and "23 DAT", respectively). Table 1 below shows the percent control of volunteer glyphosate-resistant corn compared to the untreated control.

TABLE 1

| Treatment | Actives | Rate | 9 DAT | 23 DAT |
|---|---|---|---|---|
| 1 | Untreated Control | n/a | 0 | 0 |
| 2 | Glyphosate, potassium salt | 1054 g active/hectare | 0 | 0 |
| 3 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5.6 g active/hectare | 68.78 | 6.7 |
| 4 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10.1 g active/hectare | 95.75 | 87.74 |
| 5 | Ethyl [3-[2-chloro-4-fluoro-5-(1-methyl-6-trifluoromethyl-2,4- | 20.2 g active/hectare | 99.89 | 99.89 |

TABLE 1-continued

| Treatment | Actives | Rate | 9 DAT | 23 DAT |
|---|---|---|---|---|
| | dioxo-1,2,3,4-tetrahydropyrimidin-3-yl)phenoxy]-2-pyridyloxy]acetate | | | |
| 6 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30.3 g active/hectare | 100 | 100 |
| 7 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 40.3 g active/hectare | 100 | 100 |
| 8 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5.6 g active/hectare | 98.37 | 93.64 |
| | Glyphosate, potassium salt | 1054 g active/hectare | | |
| 9 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10.1 g active/hectare | 99.56 | 99.66 |
| | Glyphosate, potassium salt | 1054 g active/hectare | | |
| 10 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 20.2 g active/hectare | 100 | 100 |
| | Glyphosate, potassium salt | 1054 g active/hectare | | |
| 11 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30.3 g active/hectare | 100 | 100 |
| | Glyphosate, potassium salt | 1054 g active/hectare | | |

As illustrated in Table 1 above, mixtures of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate (as the potassium salt) were significantly more effective at controlling glyphosate-resistant corn than either compound when applied alone. The potassium salt of glyphosate applied alone had no activity. Nine days after treatment, the mixture of the two compounds was five times as active as ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate applied alone.

Example 2

Two varieties of corn were foliarly sprayed with mixtures of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and the potassium salt of glyphosate in outdoor replicated field plots. In addition, mixtures of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glufosinate, and N,N'-dimethyl-4,4'-bipyridinium dichloride alone were foliarly sprayed. One corn variety was glyphosate-resistant and the other variety was both glyphosate and glufosinate resistant. The corn plants were at the V7 (plants with seven leaves with visible collars, about 30 to 40 inches tall) stage of development at the time of treatment. Roundup® PowerMax (available from Monsanto Company) was used as the source of the potassium salt of glyphosate. The adjuvant non-ionic surfactant was applied with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate. The effects of the treatments were observed and recorded 9 and 16 days after the treatments ("9 DAT" and "16 DAT", respectively). Table 2 below shows the percent control of glyphosate-resistant corn compared to the untreated control for corn variety P1690. Table 3 below shows the percent control of glyphosate-resistant and glufosinate-resistant corn compared to the untreated control for corn variety 765-30.

TABLE 2

| Treatment | Actives | Rate | 9 DAT | 16 DAT |
|---|---|---|---|---|
| 1 | Untreated Control | n/a | 0 | 0 |
| 2 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 1.25 g active/hectare | 16.15 | 25 |
| 3 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 2.5 g active/hectare | 49.78 | 55 |
| 4 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 g active/hectare | 44.48 | 40 |
| 5 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10 g active/hectare | 57.6 | 42.5 |
| 6 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 20 g active/hectare | 81.8 | 100 |
| 7 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30 g active/hectare | 95 | 100 |
| 8 | Glyphosate, potassium salt | 1260 g active/hectare | 0 | 0 |
| 9 | Ethyl [3-[2-chloro-4-fluoro-5-(1-methyl-6-trifluoromethyl-2,4-dioxo-1,2,3,4-tetrahydropyrimidin-3-yl) | 1.25 g active/hectare | 30.1 | 40 |

TABLE 2-continued

| Treatment | Actives | Rate | 9 DAT | 16 DAT |
|---|---|---|---|---|
| | yl)phenoxy]-2-pyridyloxy]acetate | | | |
| | Glyphosate, potassium salt | 1260 g active/hectare | | |
| 10 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 2.5 g active/hectare | 49.7 | 47.5 |
| | Glyphosate, potassium salt | 1260 g active/hectare | | |
| 11 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 g active/hectare | 64.5 | 78.5 |
| | Glyphosate, potassium salt | 1260 g active/hectare | | |
| 12 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10 g active/hectare | 83.2 | 97.5 |
| | Glyphosate, potassium salt | 1260 g active/hectare | | |
| 13 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 20 g active/hectare | 93 | 100 |
| | Glyphosate, potassium salt | 1260 g active/hectare | | |
| 14 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30 g active/hectare | 96.2 | 100 |
| | Glyphosate, potassium salt | 1260 g active/hectare | | |
| 15 | Glufosinate | 500 g active/hectare | 92.7 | 100 |
| 16 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 g active/hectare | 92.1 | 100 |
| | Glufosinate | 500 g active/hectare | | |
| 17 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10 g active/hectare | 90.7 | 100 |
| | Glufosinate | 500 g active/hectare | | |
| 18 | N,N'-dimethyl-4,4'-bipyridinium dichloride | 840 g active/hectare | 84 | 77.5 |

TABLE 3

| Treatment | Actives | Rate | 9 DAT | 16 DAT |
|---|---|---|---|---|
| 1 | Untreated Control | n/a | 0 | 0 |
| 2 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 1.25 g active/hectare | 16.15 | 25 |
| 3 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 2.5 g active/hectare | 49.78 | 52.5 |
| 4 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 g active/hectare | 42.3 | 40 |
| 5 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10 g active/hectare | 57.6 | 42.5 |
| 6 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 20 g active/hectare | 81.8 | 91.3 |
| 7 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30 g active/hectare | 95 | 100 |
| 8 | Glyphosate, potassium salt | 1260 g active/hectare | 0 | 0 |
| 9 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 1.25 g active/hectare | 30.1 | 42.5 |
| | Glyphosate, potassium salt | 1260 g active/hectare | | |
| 10 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 2.5 grams active/hectare | 43.6 | 50 |
| | Glyphosate, potassium salt | 1260 g active/hectare | | |
| 11 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 g active/hectare | 65.2 | 81.3 |
| | Glyphosate, potassium salt | 1260 g active/hectare | | |
| 12 | Ethyl [3-[2-chloro-4-fluoro-5-(1-methyl-6-trifluoromethyl-2,4-dioxo-1,2,3,4-tetrahydropyrimidin-3-yl)phenoxy]-2- | 10 grams active/hectare | 71.2 | 83.8 |

TABLE 3-continued

| Treatment | Actives | Rate | 9 DAT | 16 DAT |
|---|---|---|---|---|
| | pyridyloxy]acetate | | | |
| | Glyphosate, potassium salt | 1260 g active/hectare | | |
| 13 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 20 grams active/hectare | 89.6 | 98.8 |
| | Glyphosate, potassium salt | 1260 g active/hectare | | |
| 14 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 30 grams active/hectare | 96.3 | 100 |
| | Glyphosate, potassium salt | 1260 g active/hectare | | |
| 15 | Glufosinate | 500 g active/hectare | 3.8 | 0 |
| 16 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 5 grams active/hectare | 60.5 | 63.8 |
| | Glufosinate | 500 g active/hectare | | |
| 17 | Ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate | 10 grams active/hectare | 79 | 88.8 |
| | Glufosinate | 500 g active/hectare | | |
| 18 | N,N'-dimethyl-4,4'-bipyridinium dichloride | 840 g active/hectare | 81.3 | 92.5 |

As illustrated in Tables 2 to 3 above, mixtures of ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate (as the potassium salt) were significantly more effective at controlling glyphosate-resistant corn than either compound when applied alone. Glyphosate applied as the potassium salt alone had no activity. Sixteen days after treatment, the mixture of the two compounds were about two times as active as ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate applied alone.

Tables 1 to 3 above also show that the level of control of volunteer corn at the V4 stage was also similar at later stage of V7. These ranges of corn stage and size are the normal ranges expected when applications are made to control volunteer corn.

In addition, Examples 1 and 2 show that the synergy between ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate is not dependent upon an adjuvant. Example 1 used crop oil concentrate while Example 2 used a non-ionic surfactant.

Finally, the examples above show that ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate mixtures provide long-term synergistic activity against volunteer corn.

I claim:

1. A method for enhancing the herbicidal activity of ethyl [3-[2-chloro-4-fluoro-5-(1-methyl-6-trifluoromethyl-2,4-dioxo-1,2,3,4-tetrahydropyrimidin-3 -yl)phenoxy]-2-pyridyloxy]acetate comprising applying a synergistic mixture of ethyl [3-[2-chloro-4 -fluoro-5 -(1-methyl-6-trifluoromethyl-2,4-dioxo-1,2,3 ,4-tetrahydropyrimidin-3-yl)phenoxy]-2-pyridyloxy]acetate and glyphosate, or a salt thereof, to an area where volunteer glyphosate-resistant corn is growing, wherein the rate of application of ethyl [3 -[2-chloro-4-fluoro-5-(1-methyl-6-trifluoromethyl-2,4-dioxo-1,2,3, 4-tetrahydropyrimidin-3-yl)phenoxy]-2-pyridyloxy] acetate is from about 0.001 to about 10 grams per hectare, and the rate of application of glyphosate, or a salt thereof, is from about 1054 to about 2,000 grams per hectare.

2. The method of claim 1 wherein the glyphosate salt is selected from the group consisting of a potassium salt, a sodium salt, an isopropylamine salt, a trimesium salt, an ammonium salt, and a diammonium salt.

3. The method of claim 2 wherein the glyphosate salt is potassium.

4. The method of claim 1 wherein a glyphosate-resistant crop plant other than corn is growing in the area where the volunteer glyphosate-resistant corn is growing.

5. The method of claim 4 wherein the glyphosate-resistant crop plant is soybeans.

6. A method for controlling volunteer glyphosate-resistant corn comprising applying a synergistic mixture of ethyl [3 -[2-chloro-4-fluoro-5-(1-methyl-6-trifluoromethyl-2,4-dioxo-1,2,3,4-tetrahydropyrimidin-3-yl)phenoxy]-2-pyridyloxy]acetate and glyphosate, or a salt thereof, to an area where volunteer glyphosate-resistant corn is growing, wherein the rate of application of ethyl [3 -[2-chloro-4-fluoro-5-(1-methyl-6-trifluoromethyl-2,4-dioxo-1,2,3, 4-tetrahydropyrimidin-3-yl)phenoxy]-2-pyridyloxy] acetate is from about 0.001 to about 10 grams per hectare, and the rate of application of glyphosate, or a salt thereof, is from about 1054 to about 2,000 grams per hectare.

7. The method of claim 6 wherein the glyphosate salt is selected from the group consisting of a potassium salt, a sodium salt, an isopropylamine salt, a trimesium salt, an ammonium salt, and a diammonium salt.

8. The method of claim 7 wherein the glyphosate salt is potassium.

9. The method of claim 6 wherein a glyphosate-resistant crop plant other than corn is growing in the area where the volunteer glyphosate-resistant corn is growing.

10. The method of claim 9 wherein the glyphosate-resistant crop plant is soybeans.

11. A method for controlling glyphosate-resistant weeds comprising applying a synergistic mixture of ethyl [3-[2-chloro-4-fluoro-5-(1-methyl-6-trifluoromethyl-2,4-dioxo-1, 2,3,4-tetrahydropyrimidin-3-yl)phenoxy] -2 -pyridyloxy]acetate-and glyphosate, or a salt thereof, to an area where a glyphosate-resistant weed is growing, wherein the rate of application of ethyl [3-[2-chloro-4-fluoro-5-(1-methyl-6-trifluoromethyl-2,4-dioxo-1,2,3, 4-tetrahydropyrimidin-3-yl)phenoxy]-2-pyridyloxy] acetate is from about 0001 to about 10 grams per hectare, and the rate of application of glyphosate, or a salt thereof, is from about 1054 to about 2,000 grams per hectare.

12. The method of claim 11 wherein the glyphosate-resistant weed is selected from the group consisting of

*Lolium multiflorum*, *Amaranthus palmeri*, *Amaranthus rudis*, *Amaranthus tuberculatus*, *Ambrosia artemisiifolia*, and *Kochia scoparia*.

\* \* \* \* \*